United States Patent [19]

Jäntsch

[11] 4,166,957

[45] Sep. 4, 1979

[54] APPARATUS AND METHOD FOR PRODUCING A SECTIONAL VIEW OF A BODY

[75] Inventor: Ottomar Jäntsch, Erlangen, Fed. Rep. of Germany

[73] Assignee: Siemens Aktiengesellschaft, Munich, Fed. Rep. of Germany

[21] Appl. No.: 827,839

[22] Filed: Aug. 25, 1977

Related U.S. Application Data

[63] Continuation of Ser. No. 639,915, Dec. 11, 1975, abandoned.

[30] Foreign Application Priority Data

Dec. 17, 1974 [DE] Fed. Rep. of Germany ....... 2459665

[51] Int. Cl.² ............................................. G01N 23/00
[52] U.S. Cl. ................................................ 250/445 T
[58] Field of Search .................... 250/445 T, 370, 366, 250/320

[56] References Cited

U.S. PATENT DOCUMENTS

| | | | |
|---|---|---|---|
| 3,683,185 | 8/1972 | Muehllehner | 250/366 |
| 3,866,047 | 2/1975 | Hounsfield et al. | 250/445 T |
| 3,881,110 | 4/1975 | Hounsfield et al. | 250/445 T |
| 3,890,506 | 6/1975 | Berniger | 250/370 |

*Primary Examiner*—Bruce C. Anderson
*Attorney, Agent, or Firm*—Kenyon & Kenyon

[57] ABSTRACT

An improved apparatus and method for producing a sectional view of a body in a short time in which rays such as X-rays or gamma rays are directed in a fan shaped beam through a cross section plane of the body element in different directions and the absorption of the radiation detected by a receiver scintillator whose photons release electrons which are subsequently accelerated and then converted into electrical signals.

12 Claims, 3 Drawing Figures

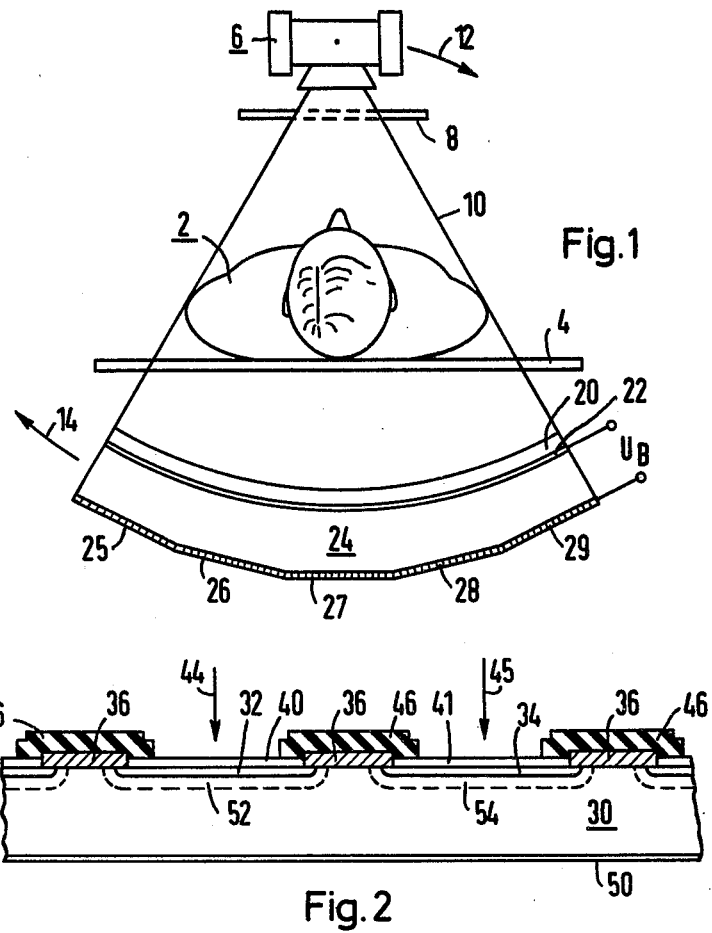
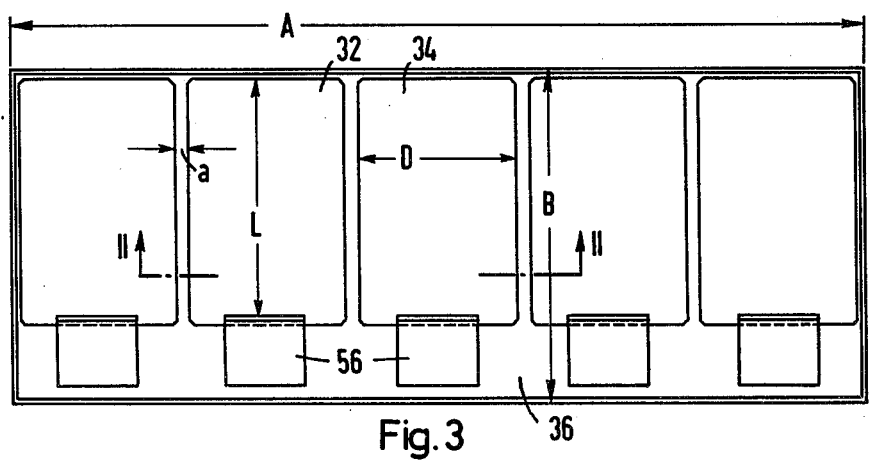
Fig. 1
Fig. 2
Fig. 3

APPARATUS AND METHOD FOR PRODUCING A SECTIONAL VIEW OF A BODY

This is a continuation of application Ser. No. 639,915 filed Dec. 11, 1975 abandoned.

BACKGROUND OF THE INVENTION

This invention relates to the production of cross sectional views of a body using ionizing radiation in general and more particularly to an improved method and apparatus for producing such a view.

Devices of this general nature in which radiation is directed through a cross-sectional plane of a body in different directions and the amount of radiation passing through the body converted into electrical signals and evaluated in an electrical storage system are known. Arrangements for carrying out such a method in which such a body is scanned by means of parallel displacement of the radiation source and the radiation receiver in the cross-sectional plane of the body are generally known as scanners.

In one known method of this type an X-ray or gamma ray source furnishes a beam of approximately parallel rays which are directed to penetrate the body to be examined in the desired cross-sectional plane. The radiation is absorbed by the body to a certain extent. The remaining radiation passes through the body. Behind the body to be examined a picture carrier is placed which the radiation strikes. Through a stepwise parallel displacement of the radiation source and picture carrier, the body elements in the cross-sectional plane are sequentially scanned. Subsequently, the radiation source and picture carrier are tilted at a predetermined angle with respect to an axis perpendicular to the cross-sectional plane and the cross-sectional plane of the body is again projected on the picture carrier by parallel displacement of the radiation source. In this manner the radiation source goes through the individual body elements in a different direction. By repeating this process several times each body element in the cross-sectional plane is imaged as often as the system is tilted about the axis. The conversion of these different individual exposures of the body elements and the correlation with the corresponding picture elements of the body cross-sectional view to be produced are obtained using an electronic computer into which are then entered, for example, 28,000 equations with 6,440 variables.

In one particular embodiment for an arrangement for carrying out such a method, the fan shaped radiation of a radiation source is subdivided using separate collimators into individual beams lying in the cross-sectional plane. By doing this the time required to obtain a sectional view is shorted. Behind the body a group of photodetectors are located with which a common reference scintillator having a light tube is associated. The output signals of these photodetectors or photomultipliers are further processed in electronic circuitry and then control a printer which furnishes a sectional view of the body. Such as disclosed in German Offenlegungsschrift No. 1,941,433. In this arrangement there is a stationary source for this scanning. The spaces between the individual photodetectors with the associated collimators are covered by an appropriate movement of the photo detectors.

Although this method and apparatus for producing such views is satisfactory it suffers from a number of disadvantages. In the first instance it takes too long. Some portions of the human body are always in motion and the previous method does not permit producing accurate pictures of those parts. Furthermore, the prior method suffered from a lack of resolution. To obtain good resolution with this prior arrangement an excessive equipment cost is required. A further serious disadvantage of the method was the amount of total radiation received by a human body being examined. Since a number of exposures were made the body was exposed to the radiation each time. Although it would be possible to increase the number of detectors in these prior art arrangements while decreasing their receiving area at the same time, this would require a corresponding increase in the power of the radiation source in order to obtain useful signals with an adequate signal to noise ratio, since, with the prior art photodetectors, relatively small signal to noise ratios are available. Very likely the radiation would have to be increased to an amount above that to which the human body should be exposed.

In view of these difficulties, the need for an improved system which can operate quickly, give good resolution and not subject the human body to large radiation doses becomes evident.

SUMMARY OF THE INVENTION

The present invention provides such a method and apparatus. The present invention starts out with a fan shaped beams of rays arranged to go through the body in a cross-sectional plane to be examined. A receiver is placed behind the body and includes a scintillator onto which the fan shaped beam is directed. The photons of the scintillator release electrons which are then accelerated and converted into corresponding electrical signals. With this method, the subdivision of the sectional plane of the body to provide individual picture elements takes place in the radiation receiver.

Through the use of an image converter principle along with detectors for electrons, a sufficient signal to noise ratio is obtained without increased radiation power even if the packing density of the detectors is high, i.e., even with the multiciplity of detectors each having a relatively small receiving area. By accelerating the electrons with a corresponding increase in power, a gain of more than one to one thousand can in general be obtained. As a result the radiation power of the source and thus the radiation dose received by the cross-section of the body of which a view is to be produced can be reduced. Since all of the electric signals associated with the fan shaped beam are formed and are detected simultaneously, scanning of the cross-sectional plane of the body is no longer necessary.

A solid state image converter can be used for accelerating the electrons. Preferably a vacuum image converter in which the electrons released from a photo cathode are accelerated in a vacuum space using an applied voltage of, for example, 20 KV will be used. The accelerated electrons will strike the detector system preferably containing space resolving semiconductor detectors.

It is known in the art that gamma rays can be made visible by converting the gamma quanta into electron beams and conducting the electron beams to a space resolving detector arrangement. A conversion of the gamma ray picture into the corresponding electron image is accomplished using a vacuum image converter whose input target contains a scintillator-photo cathode combination and its output target contains the space resolving detector. This may be designed as a linear detector such as disclosed in German Offenlegungsschrift No. 2,055,824. In such an arrangement the image converter, in conjunction with the linear detector, furnishes an image. A particular embodiment of such a space resolving detector arrangement in linear form is known which has barrier layer electrodes exposed to the arriving radiation which are made by a planar technique and arranged on a silicon semiconductor body having high resistivity. The electrodes which receive the radiation are made by diffusion of doping material into a thin surface layer. The end zone of the electrodes, where the barier layer comes to the surface, is covered by an oxide layer. This is disclosed in German Offenlegunsschrift No. 2,235,680.

The arrangement used for implementing the present invention deviates from this arrangement in that the barrier layer electrodes arranged on a common semiconductor body are combined with a common, barrier free electrode arranged on the opposite, flat side to form the detector unit. The barrier layer electrodes, which are preferably made using a planar technique, are exposed to the electrode beams from the photocathode of an electronic vacuum image convertor whose scintillator is used as the radiation receiver of the X-rays or gamma rays. The electrons emminating from the photocathode are accelerated by an applied voltage and generate, in the field zone of the detector between the barrier layer electrode and the essentially barrier free electrode, pairs of electrons and holes whose current is proportional to the intensity of the arriving rays.

A large number of detector units are used to form the detector system. Typically several hundreds of such detectors will be used. The entire fan shaped X-ray beam penetrating the body to be examined is then receiving by the detector system simultaneously. Since the area of each of the individual barrier layer electrodes in the detector system is at most a few milimeters wide, a subdivision of the sectional plane of the body into a large number of lines and therefore imaging with correspondingly high resolution is obtained.

Although the radiation time for the body to be examined is relatively short, the radiation appears at the detector system as a continuous flow of rays generating a corresponding signal current. This signal current, which provides the useful signal, must be far above the cut-off current appearing as a dark current and must thus be limited accordingly. In order for the detector effect to come about, a sufficiently large space charge zone, disposed in front of the barrier layer electrode, is necessary. The size of the space charge zone increases with the resistenance of the semiconductor material for a given cut-off voltage. However, the cut-off current increases at the same time. With a a small cut-off current a sufficient space charge zone can be obtained if the semi conductor body has a resistivity of about 3–300 om-cm and more particularly between 10 and 100 om-cm.

The space charge zone is determined, for a given conductance type of semiconductor material, not only by the resistance of the semiconductor body but also by the applied voltage. This can be between 0 and 10 volts and in particular will be between 0 and 1 volt. If the applied voltage is 0, a diffusion voltage which is less than 1 volt is present at the p-n junction of the barrier layer electrode. The variables mentioned are chosen so that the thickness of the space charge zone is between 1 and 10 $\mu$m and more particularly 2 and 5 $\mu$m.

BRIEF DESCRIPTION OF THE DRAWINGS

FIG. 1 is an elevation view of the overall arrangement for carrying out the method of the present invention.

FIG. 2 is a cross-sectional view of a portion of a dector unit according to present invention.

FIG. 3 is a plan view of the detector of FIG. 2.

DETAILED DESCRIPTION

As illustrated by FIG. 1 a human body 2 is placed on a table 4 and has disposed thereabove a radiation source 6 for ionizing radiation, preferably an X-ray tube. In accordance with the present invention, it is desired to make a cross-sectional picture of the human body 2. The radiation source includes a conventional collimator 8, shown simply as a diaphram on the figure, which developes a fan shaped beam of rays which penotrate the body to in a cross-sectional plane. In general, the collimator 8 forms part of the radiation source and can be arranged in its housing.

The fan shaped beam of radiation 10 penetrates the body 2 in the sectional plane being measured and is absorbed differently by different components of the body. The portion of the rays not absorbed strike a scintillator 20. The scintillator 20 can include a carrier of glass or metal containing a luminiscant layer of alkyl halogenide, particularly cesium iodide with one or more activators. These are advantageously applied to the carrier by evaporation in a vacuum. The single layer may also be made of fibers or needles arranged perpendicular to the carrier; such can be prepared by repeated evaporation. The arriving radiation 10 is absorbed by the scintillator and releases photons which releases electrons in the light sensitive layer of a photo-cathode 22. The photocathode 22 will preferably be a cesium-antimony compound. The electrons are directed from here toward the detector system 24. In the space between the detector system and the photocathode 22 they are accelerated by an applied acceleration voltage $U_B$ of, for example 20 kV and their energy increases correspondingly. The high energy electrons then impinge on the barrier layer electrodes of the semiconductor detectors. In the individual semiconductors detectors, the electrons are multiplied by a gain factor which results from the quotient of the applied accelerating voltage and the pair formation energy of silicon of 3.6 eV. If the semiconductor detectors have a voltage stress in the cut off direction, an electron current is obtained which is a prortional to the intensity of the arriving radiation.

As noted above a large number of individual semiconductors are used. Of these, large groups can be arranged on a common semicomductor body which will preferably be silicon. For example, 10 or as few as 5 can be arranged on a single body. These detector units are indicated on FIG. 1 by the reference numerals 25–29. The figure shows the units separated into individual detectors. The groups of detectors on common semiconductor bodies are then arranged in a polygonal form as illustrated on the drawing to approximate the arc of the circle. The center of this arc is at the anti cathode of the radiation source 6.

The entire radiation receiver can also be designed so that the image of the radiation 10 is reduced electron-optically by at least one order of magnitude e.g., in the ration of 1 to 13.

The electrical signals supplied by the individual detectors can be directly evaluated in a storage and computer combination and fed to an image display device or printing device which prints the sectional view of the body in accordance with the signals provided.

After one exposure the radiation source and receiver are tilted in the direction of the arrows 12 and 14, about an axis perpendicular to the sectional plane of the body and not specifically shown in the figure, by a predetermined angle and further if radiation of the body 2 takes place with the resulting signals evaluated.

FIG. 2 is a longitudinal cross section through a portion of one of the detector units 25-29 of FIG. 1. A common semiconductor body with the thickness of, for example 300 $\mu$m which will preferably be n-conduction silicon with a resistivity of 10 to 100 ohm-cm is used. On its upper surface, electrodes 32 and 34 for receiving electrons are formed by the diffusion of p conduction doping material, particularly boron. These are diffused into window like openings of an oxide layer 36. The barrier layer between the diffused electrode and the silicon in all cases comes to the surface below the oxide layer 36. This oxide, in conventional fashion, can be a layer of silicon dioxide, $SiO_2$ formed in-conventional fashion. During the diffusion process a thin glass layer 40 or 41 is formed over the electrode 32 or 34. This will not impede the passage of the electron beams indicated on the figure by the arrows 44 and 45. This glass layer need not be removed since the rays can easily pass therethrough. The only place where it must be removed is at a point where electrical contact leads are connected to the electrodes 32 and 34. These contact points are shown in FIG. 3 to be described below. It is advantageous if the oxide layer 36 has an additional protective layer 46 which may be a heat resistance plastic material such as polymide. The polymide layer protects the thin oxide layer which will typically only be about 0.6 $\mu$m thick and whose thickness generally will not substantially exceed 1 $\mu$m. In addition, the protective layer 46 protects the barrier layer which comes to the surface of the semiconductor 30 against the effects of harmful vapor, e.g., of cesium or potassium during the manufacture of the photocathode 22 of the image converter.

At the lower plane surface the semiconductor is provided which a barrier free metal electrode 50. In some circumstances only a relatively small portion of the lower plane side of the semiconductor 30 need have this electrode thereon. In some instances it may even be possible to place this on the lateral surfaces of the semiconductor body 30 which are not shown in the figure. The electrode 50 or portions thereof may also consist of surface layers of the semiconductor with increased electrical conductivity.

A voltage is applied between the electrodes 32 or 34 and 50 and is chosen so that the space charge or field zone in front of the electrodes is substantially larger than the diffusion depth of the electrodes 32 and 34. This diffusion depth is generally less than 1 $\mu$m and more commonly in the order of 0.3 $\mu$m. A depth of the space charge zone indicated as 52 and 54 on the figure, the boundary layer of which is indicated by the dashed lines is in general substantially more than 1 $\mu$m, e.g., 5 to 10 $\mu$m. With such an arrangement of the detectors, a signal current for the detectors of $2\times10^{-6}$ A is obtained. With a dark current for the detectors of about $5\times10^{-9}$ A, a very good signal to noise ratio is obtained. It is a particular advantage of this arrangement in carrying out the above method that the detector system 24 can be operated at room temperature without special cooling because the amplification takes place ahead of the detectors in the image converter.

A plan view of the detector arrangement is shown on FIG. 3. Once again the oxide layer 36 on top the semiconductor body is shown as are the barrier layer electrodes 32 and 34 along with three unnubered similar electrodes. Each of the electrodes has an active length L of only a few milimeters, e.g., 8 mm and even a small active width D of, for example, 6 mm. The electrodes are spaced at a distance a of, for example, 0.5 mm from each other. The detector unit will have an overall width B of about 11 mm and a total length A of, for example, 33 mm. At each of the electrodes 32 or 34 the boron glass layer 40 shown on FIG. 2, but not specifically indicated on FIG. 3, is provided with an opening into which a conductor 56, for example of a metal such as aluminum, is brought into contact with the respective electrode.

It is possible to deviate from the arrangement shown in figure and to make the detector system 24 such that the different detector units 25 through 29 are arranged side by side such that all electrodes lie in one plane. In such a case the difference in the share of the radiation caused by the angle of incidence can be compensated by using electrodes with correspondingly different active widths D. The active width of the electrode 34 of the center detector will then be made smaller than the active width of the adjacent electrodes. The outermost electrodes will than have the largest width. Such may also be done in the individual straight line segments of the detector, i.e., the sections 25-29 of FIG. 1. In other words, the electrodes 32 or 34 can be made different widths to correspond for the deviation of the straight line segment from an arcuate section.

Instead of using an n-conduction semiconductor body, a body of p-conduction silicon may also be used. In such a case the resistivity of the material should be an order of magnitude larger, i.e., in the range of 10 to 900 ohm-cm; and more particularly 30 to 300 ohm-cm. In such a case the barrier layer electrodes such as the electrodes 32 and 34 will be n-conducting and can be prepared, for example, by the diffusion of phosphrous.

The method of the present invention is quite well suited for producing sectional views of bodies of living beings. However, it can also be used for examining inanimate objects such as is done in nondestructive testing of materials.

In the example given the method is implemented using a vacuum image converter for the conversion and amplification of the radiation. The same effect can also be obtained using a solid state image converter. These and other modifications may be made without departing from the spirit of the invention which is intended to be limited solely by the intended claims.

I claim:

1. In a method for producing a sectional view of a body in which the picture elements are derived from the absorption of ionizing rays going through the corresponding body element in a cross-sectional plane in different directions with the degree of absorption converted into electrical signals and the signals evaluated to develop outputs which are then provided to a display device, the improvement comprising:

(a) irradiating the body of which a sectional view is to be produced with a fan shaped beam of radiation arranged to penetrate the body in the cross sectional plane to be examined;

(b) disposing a vacuum image converter including a scintillator and photo-cathode behind the body as a receiver to detect the degree of absorption, said vacuum image converter including a plurality of detector units disposed side by side in the sectional plane to be measured in a polygonal form to approximate the arc of the circle, each detector unit comprising a plurality of space resolving semiconductor detectors formed on a common, thin semiconductor body;

(c) accelerating the electrons in the vacuum; and (d) multiplying and converting the accelerated electrons into electrical signals in a space resolving manner using said semiconductor detectors.

2. In apparatus for producing a sectional view of a body in which picture elements are derived from the absorption of ionizing rays passing through the body elements in a cross-sectional plane in different directions and in which the absorption is converted into electrical signals which are electronically evaluated and the results of the evaluation provided to a display device, an improved arrangement for quickly and efficiently obtaining a plurality of electrical signals corresponding to individual picture elements with a small amount of radiation comprising:

(a) means for generating a fan-shaped beam of radiation; and (b) an electronic vacuum image converter including:
  i. a scintillator and photocathode acting as a radiation receiver and releasing photoelectrons in response to incident radiation;
  ii. means to accelerate the photoelectrons eminating from said scintillator and photocathode in the vacuum within said image converter; and
  iii. a detector system comprising a plurality of detector units disposed side by side in the sectional plane to be measured in a polygonal form to approximate the arc of the circle, each detector unit comprising a thin semiconductor body having formed thereon a plurality of space resulting semiconductor detectors, for decellerating and multiplying said accelerated photoelectrons, the output of said semiconductors being the electrical signals which are to be electronically evaluated.

3. Apparatus according to claim 2 wherein said image converter is an electronic vacuum image converter having a scintillator for receiving the fan shaped beam of rays and a photo-cathode responsive thereto for producing electrons which are directed toward said detector system.

4. Apparatus according to claim 2 wherein said semiconductor detector system comprises a plurality of semiconductor detectors each comprising:
  (a) a silicon semiconductor body;
  (b) a diffused barrier layer electrode on one side of said semiconductor body; and
  (c) an oxide layer covering the barrier between said diffused electrodes and said semiconductor body where it comes to the surface of said one side.

5. Apparatus according to claim 4 wherein a plurality of barrier layer electrodes are arranged side by side on a common silicon semiconductor body to form a detector unit and further including a common barrier free electrode on the opposite plane side of said silicon semiconductor body.

6. Apparatus according to claim 5 wherein said detector system is made up of a plurality of detector units disposed in the sectional plane to be measured side by side.

7. Apparatus according to claim 4 wherein said silicon semiconductor body is an n-conduction silicon semiconductor with a resistivity of between 3 and 300 ohm-cm.

8. Apparatus according to claim 4 wherein said semiconductor body is a p-condition silicon semiconductor with a resistivity between 9 and 900 ohm-cm.

9. Apparatus according to claim 4 wherein the depth of the space charge zone behind each of said barier layer electrodes is between 1 and 10 $\mu$m.

10. Apparatus according to claim 4 and further including a protective layer over said oxide layer.

11. Apparatus according to claim 5 wherein said barrier layer electrodes are made with different widths.

12. Apparatus according to claim 3 wherein said detector system and vacuum image converter are arranged to reduce the image of the radiation electron optically at least one order of magnitude.

* * * * *